United States Patent [19]

Sanchez

[11] Patent Number: 5,296,628
[45] Date of Patent: Mar. 22, 1994

[54] PREPARATION OF 6-AMINOCAPRONITRILE

[75] Inventor: Kathryn M. Sanchez, West Chester, Pa.

[73] Assignee: E. I. Du Pont de Nemours and Company, Wilmington, Del.

[21] Appl. No.: 836,782

[22] Filed: Feb. 13, 1992

[51] Int. Cl.$^5$ ............................................ C07C 255/03
[52] U.S. Cl. ................................... 558/452; 558/459
[58] Field of Search ............................... 558/452, 459

[56] References Cited

U.S. PATENT DOCUMENTS 2,208,598  7/1940  Rigby ................................. 558/452
4,248,799  2/1981  Drake ................................. 564/491

OTHER PUBLICATIONS

CA76(19):112740s E-Aminocapronitrile, Senoo et al., p. 445, 1972.
CA114(8):71087s The Electrochemical . . . azelanitrile, Song, p. 599, 1991.
CA115(22):235168t Activity . . . hydrogenation, Medina et al., p. 172, 1991.

Primary Examiner—Mary C. Lee
Assistant Examiner—Joseph K. McKane

[57] ABSTRACT

A process for the conversion of adiponitrile to 6-aminocapronitrile in high yield and high selectivity using Raney nickel catalyst and a reaction mixture containing a low valent transition metal complex.

6 Claims, No Drawings

PREPARATION OF 6-AMINOCAPRONITRILE

FIELD OF THE INVENTION

This invention relates to the preparation of 6-aminocapronitrile by the catalytic hydrogenation of adiponitrile.

BACKGROUND OF THE INVENTION

6-Aminocapronitrile is disclosed in Greenewalt U.S. Pat. No. 2,245,129 as a monomer that may be polymerized to form high molecular weight polymer. Catalytic polymerization of this monomer is disclosed in U.S. Pat. No. 4,568,736 to Curatolo et al.

A process for the preparation of 6-aminocapronitrile by the hydrogenation of adiponitrile using a nickel catalyst is disclosed in U.S. Pat. No. 2,208,598 to Rigby. The highest yield reported in the patent is 52%.

Drake U.S. Pat. No. 4,248,799 discloses the hydrogenation of nitriles using Raney cobalt or Raney nickel promoted with a Group VIB metal. Specific examples mentioned are elemental chromium, chromium acetate, chromium chloride, chromium oxide, elemental molybdenum, molybdenum hydroxide, molybdenum oxide, elemental tungsten, tungsten chloride, tungsten oxide, and mixtures of two or more of these.

It is the object of the present invention to provide a process for the preparation of 6-aminocapronitrile from adiponitrile in high yield and high selectivity.

SUMMARY OF THE INVENTION

The present invention is a process for the production of 6-aminocapronitrile by the hydrogenation of adiponitrile which comprises forming a reaction mixture containing (a) adiponitrile, (b) a base selected from the group consisting of sodium hydroxide, lithium hydroxide, potassium hydroxide, and ammonium hydroxide, (c) hydrogen, (d) a low valent transition metal complex selected from the group consisting of chromium hexacarbonyl, tungsten hexacarbonyl, dibenzene chromium, dicobalt octacarbonyl, chromium (III) acetate, cobalt (II) acetate, and iron (III) acetylacetonate and (e) a Raney nickel catalyst and reacting said mixture at a hydrogen pressure of between about 200 and 1000 psi at a temperature about 50 to 90 degrees C.

The process may be carried out using the catalyst in a slurry form. Alternatively the catalyst may be a fixed bed catalyst. If the catalyst is in slurry form it is usually present in the reaction mixture in the amount of about 3 to 30% by weight of the reaction mixture. In order to keep the catalyst in a slurry form it is stirred while the reaction is taking place.

The amount of low valent transition metal complex usually will be in the range of about 0.1 to 3% by weight of the reaction mixture.

The reaction mixture may contain a solvent for other components of the mixture. Lower alkyl alcohols such as methanol, ethanol, and propanol and hydrocarbons such as hexane and toluene are suitable. Solvent may be present in the mixture in amounts up to about 90% by weight of the mixture.

DETAILED DESCRIPTION OF THE INVENTION

By using the process of the present invention the desired product, 6-aminocapronitrile, is obtained in high yield and in high selectivity. Because of the high selectivity, the purification of the product is simplified. Only small amounts of by-product are formed; so the purification essentially consists of separation of 6-aminocapronitrile from adiponitrile.

The Raney nickel catalyst may be treated with the low valent transition metal complex prior to introducing the other components of the reaction mixture, or the Raney nickel may be mixed with the other components of the reaction mixture, including the metal complex. It is believed that the metal complex acts on the Raney nickel and modified its properties resulting in a catalyst that is more selective in the hydrogenation of adiponitrile yielding more 6-aminocapronitrile in greater selectivity.

The hydroxide in the reaction mixture should be present in the amount of about 0.1 to 5% by weight of the reaction mixture.

EXAMPLES

Control Example A (Not an example of this invention)

A reactor was charged with 150 cc of methanol, 15 g of adiponitrile, 0.50 g of lithium hydroxide, 5 g of Raney nickel catalyst. The reaction was run at 500 psig hydrogen at 65 degrees C. The reactor was stirred at a rate of 1500 rpm. The yield was 54%. The conversion was 88% and the selectivity to 6-aminocapronitrile was 61%.

Control Example B (Not an example of this invention)

A reactor was charged with 5 g of commercial chromium and iron promoted Raney nickel catalyst, 150 cc of methanol, 15 g of adiponitrile, 0.50 g of lithium hydroxide. The reaction was run at 500 psig hydrogen at 65 degrees C. The reactor was stirred at a rate of 1500 rpm. The yield of 6-aminocapronitrile was 61%, at a conversion of 94% and a selectivity to 6-aminocapronitrile of 65%.

EXAMPLE 1

A reactor was charged with 5 g of the same Raney nickel catalyst as Control Example A, 150 cc of methanol, 15 g of 6-aminocapronitrile, 0.50 g of lithium hydroxide, and 2.5 g of $Cr(CO)_6$. The reaction was run at 500 psig hydrogen at 65 degrees C. and stirred at 1500 rpm. The conversion was 85%, selectivity to 6-aminocapronitrile was 92%. At adiponitrile conversion of less than 70%, the selectivity to 6-aminocapronitrile was 100%.

EXAMPLE 2

The process of Example 1 was repeated except that 1.4 g of 50% aqueous sodium hydroxide was substituted for the lithium hydroxide, and 0.59 g of $W(CO)_6$ was substituted for the $Cr(CO)_6$, and 7.5 g of Raney nickel catalyst was used instead of 5 g. The yield of 6-aminocapronitrile was 84%. At a conversion of 96%, selectivity was 88%. At a conversion of less than 60%, the selectivity of 6-aminocapronitrile was 100%.

EXAMPLE 3

A reactor was charged with 150 cc of hexane, 6.0 g of Raney nickel and 1.0 g of $Cr(CO)_6$. This mixture was stirred under 500 psig hydrogen at 65 degrees C. The reactor was cooled and the hydrogen vented and 1.4 g of 50% aqueous sodium hydroxide and 15 g of adiponitrile added. The reaction was performed in the same manner as the previous examples, but allowed to run to only 45% conversion. At this conversion, the selectivity to 6-aminocapronitrile was 100%.

EXAMPLE 4

The reactor was charged with 150 cc of methanol, 15 g of adiponitrile, 1.6 g of 50% aqueous sodium hydroxide, 0.68 g of $Co_2(CO)_8$ and 7.3 g of Raney nickel. The reaction was run at 500 psig hydrogen at 65 degrees C. with a stirring rate of 1500 rpm. The yield of 6-aminocapronitrile was 79%. At a conversion rate of 92%, the selectivity to 6-aminocapronitrile was 86%.

I claim:

1. A process for the production of 6-aminocapronitrile by the hydrogenation of adiponitrile which comprises forming a reaction mixture containing (a) adiponitrile, (b) a base selected from the group consisting of sodium hydroxide, lithium hydroxide, potassium hydroxide, and ammonium hydroxide, (c) hydrogen, (d) a low valent transition metal complex selected from the group consisting of chromium hexacarbonyl, tungsten hexacarbonyl, dibenzene chromium, dicobalt octacarbonyl, chromium (III) acetate, cobalt (II) acetate, and iron (III) acetylacetonate, and (e) a Raney nickel catalyst and reacting said mixture at a hydrogen pressure of between about 200 and 1000 psig and at a temperature of about 50 to 90 degrees C.

2. The process of claim 1 in which the catalyst is a slurry and is present in the reaction mixture in the amount of about 3 to 30% by weight of the reaction mixture.

3. The process of claim 1 in which the reaction mixture is stirred while it is reacting.

4. The process of claim 2 in which the amount of metal complex is 0.1 to 3% by weight of the reaction mixture.

5. The process of claim 1 in which the catalyst is in a fixed bed.

6. The process of claim 1 in which the reaction mixture contains a lower alkyl alcohol solvent.

* * * * *